United States Patent [19]

Coward

[11] Plant 4,640

[45] Feb. 3, 1981

[54] CHRYSANTHEMUM PLANT

[76] Inventor: Bob G. Coward, P.O. Box 1608, Ft. Myers, Fla. 33902

[21] Appl. No.: 68,403

[22] Filed: Aug. 21, 1979

[51] Int. Cl.[3] ..... A01H 5/00

[52] U.S. Cl. ..... Plt./82

[58] Field of Search ..... Plt./82

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant with flat decorative capitulum which is a sport of Bronze Belair disclosed in U.S. Plant Pat. No. 3,183. The new cultivar is distinguished from other cultivars of the Belair family by its dark red-bronze ray floret color.

1 Drawing Figure

1

The present invention comprises a new and distinct cultivar of *Chrysanthemum morifolium,* Ramat., hereafter referred to by the cultivar name of Red Belair.

Red Belair is a spontaneous mutation of Bronze Belair, disclosed in U.S. Plant Pat. No. 3,183, and was selected to expand the color range of the Belair family. Red Belair was discovered and selected in a cultivated area by Bob G. Coward on May 10, 1977 as one plant in Fort Myers, Fla. The first act of asexual reproduction of Red Belair was accomplished when vegetative cuttings were taken from the initial selection in Fort Myers, Fla. by Bob G. Coward.

Continued asexual reproduction by vegetative cuttings for evaluative flowering tests in conjunction with horticultural examination of selected units initiated Apr. 16, 1979 has demonstrated that the combination of characteristics as herein disclosed for Red Belair are firmly fixed and are retained through successive generations of asexual reproduction. Red Belair has not been observed under all possible environmental conditions. The phenotype may vary significantly with variations in environment such as temperature, light intensity and daylength. The following observations, measurements and comparisons describe plants grown in Fort Myers, Fla. under environmental conditions which approximate those generally used in commercial practice.

The following traits have been repeatedly observed and are determined to be basic characteristics of Red Belair which in combination distinguish this chrysanthemum as a new and distinct cultivar:

(1) decorative capitulum type;

(2) flat capitulum form;

(3) dark red-bronze ray floret color;

(4) diameter across face of inflorescence ranging from 75 to 90 mm. at maturity;

(5) uniform nine week photoperiodic flowering response to short days;

(6) tall plant height (attaining a height as a flowered plant of 70–75 cm. from a rooted cutting planted to short days and grown as a single stem plant for April through November flowerings); and (7) semi-upright branching pattern.

The accompanying color photographic drawing shows typical inflorescence and foliage characteristics of Red Belair with the colors being as nearly true as possible with photographic drawings of this type.

Of the many commercial cultivars known to the present inventors the most similar in comparison to Red Belair is the cultivar Flame Belair.

2

Reference is made to attached Chart A which compares certain characteristics of Red Belair with the same characteristics of Flame Belair. In comparison to Flame Belair, the ray floret color of Red Belair is more red (less yellow). Other characteristics of Red Belair are similar to the same characterists of Flame Belair.

In the following description, color references are made to The Royal Horticultural Society Colour Chart. The color values were determined between 9:30 and 10:00 A.M. on June 1, 1979 under 100 foot-candle light intensity at Salinas, Calif.

Classification:

*Botanical.*—*Chrysanthemum morifolium,* Ramat., cv Red Belair.

*Commercial.*—Cut decorative spray.

I. Inflorescence:

A. *Capitulum.*—Form: flat. Type: decorative. Diameter across face: 75 to 90 mm.

B. *Corolla of ray florets.*—Color (general tonality): 46-A over 34-A. Color (abaxial): base color 34-A overlaid with 46-A, to 34-A overlaid with 46-B, dulling with age to 34-D overlaid with 42-B. Color (adaxial): 46-A over 10-B, oxidizing to 46-B streaked lightly over 10-D. Shape: flat liqulate, developing moderate reverse roll along margins with maturity.

C. *Reproductive organs.*—Androecium: present disc florets only; numerous; scant to no pollen. Gynoecium: present both ray and disc florets.

II. Plant:

A. *General appearance.*—Height: tall. Branching pattern: semi-upright.

B. *Foliage.*—Color (abaxial): approximately 147-A. Color (adaxial): approximately 147-B overlaid with 147-C. Shape: moderately lobed and coarsely serrated.

I claim:

1. A new and distinct cultivar of *Chrysanthemum morifolium,* Ramat., known by the cultivar name Red Belair and particularly characterized as to uniqueness by the combined characteristics of decorative capitulum type; flat capitulum form; dark red-bronze ray floret color; diameter across face of capitulum from 75 to 90 mm. at maturity; uniform nine week response to photoperiodic short-day control; tall plant height; and semi-upright branching pattern.

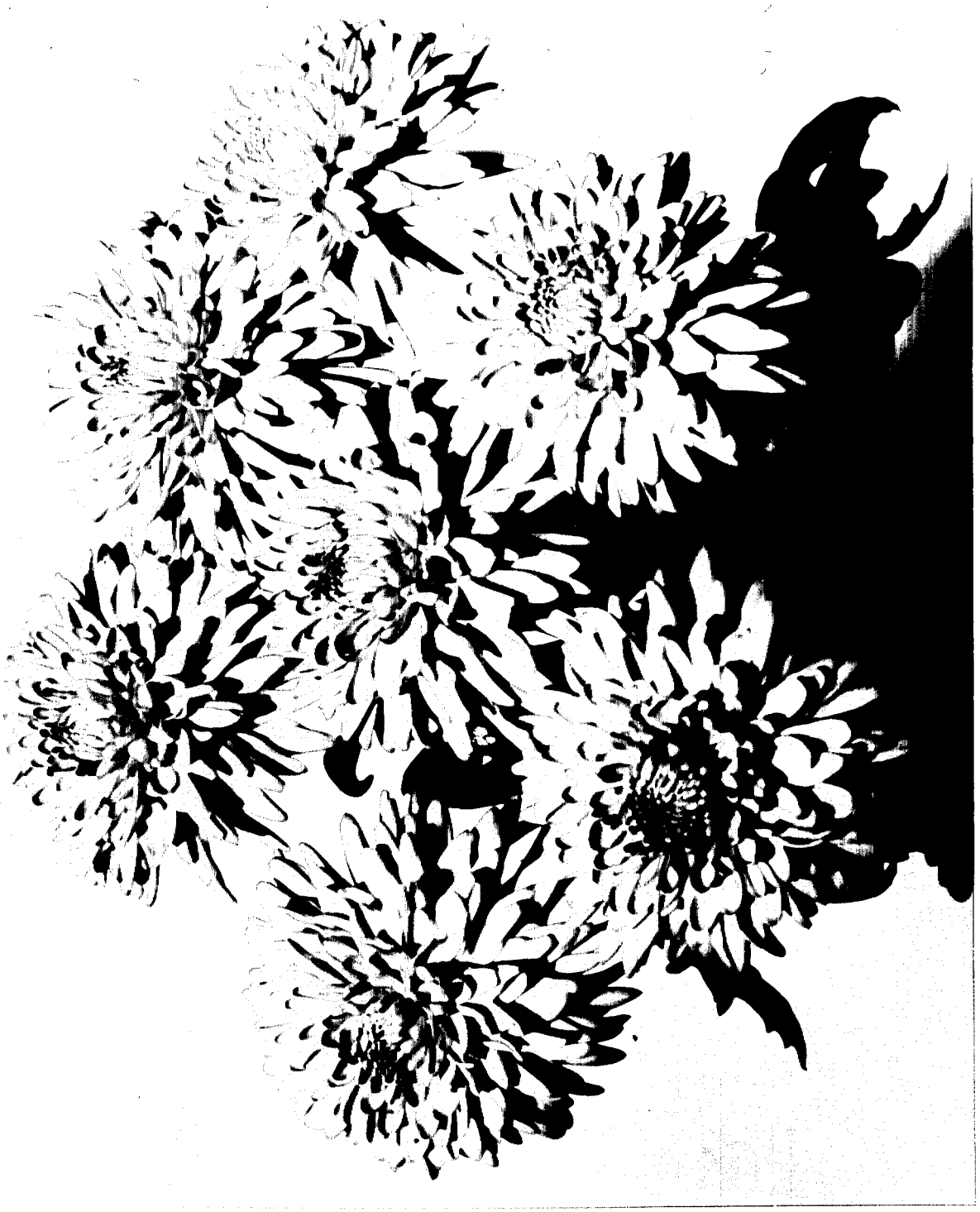

* * * * *